United States Patent

Campbell et al.

(10) Patent No.: US 6,498,166 B1
(45) Date of Patent: Dec. 24, 2002

(54) PYRAZOLOPYRIDINES

(75) Inventors: Ian Baxter Campbell, Stevenage (GB); Paul Francis Lambeth, Stevenage (GB); Alan Naylor, Stevenage (GB); Neil Anthony Pegg, Birmingham (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/890,925

(22) PCT Filed: Dec. 22, 1999

(86) PCT No.: PCT/EP99/10263

§ 371 (c)(1),
(2), (4) Date: Aug. 30, 2001

(87) PCT Pub. No.: WO00/52008

PCT Pub. Date: Sep. 8, 2000

(30) Foreign Application Priority Data

Feb. 27, 1999 (GB) ............ 9904506
Sep. 3, 1999 (GB) ............ 9920904

(51) Int. Cl.[7] ............ A61K 31/437; C07D 471/04; A61P 29/00
(52) U.S. Cl. ............ 514/300; 546/121
(58) Field of Search ............ 546/121; 514/300

(56) References Cited

U.S. PATENT DOCUMENTS

| | | |
|---|---|---|
| 4,985,444 A | 1/1991 | Shiokawa et al. |
| 5,155,114 A | 10/1992 | Shiokawa et al. |
| 5,296,490 A | 3/1994 | Shiokawa et al. |
| 5,300,478 A | 4/1994 | Michaely et al. |
| 5,498,774 A | 3/1996 | Mitsudera et al. |
| 5,552,422 A | 9/1996 | Gauthier et al. |
| 5,700,816 A | 12/1997 | Isakson et al. |
| 5,990,148 A | 11/1999 | Isakson et al. |
| 6,136,839 A | 10/2000 | Isakson et al. |

FOREIGN PATENT DOCUMENTS

| | | |
|---|---|---|
| EP | 0364204 A1 | 4/1990 |
| EP | 0404190 A1 | 12/1990 |
| EP | 0404190 B1 | 12/1990 |
| EP | 0467248 B1 | 1/1992 |
| WO | WO 9100092 | 1/1991 |
| WO | WO 9119497 | 12/1991 |
| WO | WO 9500501 | 1/1995 |
| WO | WO 9606840 | 3/1996 |
| WO | WO 9621667 | 7/1996 |
| WO | WO96 31509 A | 10/1996 |
| WO | WO 9641625 | 12/1996 |
| WO | WO9641626 | 12/1996 |
| WO | WO 9641645 | 12/1996 |
| WO | WO 9912930 | 3/1999 |
| WO | WO 0114375 A1 | 3/2001 |

OTHER PUBLICATIONS

Talley, John J., *Ashley Publications Ltd.*, ISSN 1354–3776, 7(1): (1997), pp. 55–62.
Talley, John J., *Progress in Medicinal Chemistry*, vol. 36, (1999); pp. 201–234.
Carter, Jeffery S., *Ashley Publications Ltd.*, ISSN 1354–3776, vol.8(1): (1998), pp. 21–29.
Vane, John, *Nature*, vol. 367: (1994) pp. 215–216.
Roy, P., A New Series of Selective Cox–2 Inhibitors: 5,6–Diarylthiazolo [3,2–b][1,22,4] Triazoles, *Bioorganic & Med. Chem. Ltrs*, vol. 7, No. 1, 1997, pp. 57–62.
Therien, Michael, Synthesis and Biological Evaluation of 5,6–Diarylimidazo[2.1–b]Thiazole As Selective Cox–2 Inhibitors, *Bioorganic& Med. Chem. Ltrs*, vol. 7, No. 1, 1997, pp. 47–52.
Akahane, Atsushi, Discovery of 6–Oxo–3–(2–Phenylpyrazolo[1,5–a] pyridin–3–yl)–1(6H)–pyridazinebutanoic Acid (FR 838): A Novel Non–Xanthine Adenosine $A_1$ Receptor Antagonist with Potent Diuretic Activity, *Journal of Medicinal Chemistry*, vol. 42, No. 5, 1999, pp. 779–783.

*Primary Examiner*—Evelyn Mei Huang
(74) *Attorney, Agent, or Firm*—Lorie Ann Morgan

(57) ABSTRACT

The invention provides the compounds of formula (I)

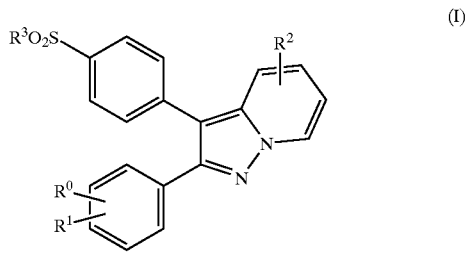

wherein:
$R^0$ and $R^1$ are independently selected from H, halogen, $C_{1-6}$alkyl, $C_{1-6}$alkoxy, or $C_{1-6}$alkoxy substituted by one or more fluorine atoms;
$R^2$ is halogen, CN, $CONR^4R^5$, $CO_2H$, $CO_2C_{1-6}$alkyl, or $NHSO_2R^4$;
$R^3$ is $C_{1-6}$alkyl or $NH_2$; and
$R^4$ and $R^5$ are independently selected from H, $C_{1-6}$alkyl, phenyl, phenyl substituted by one or more atoms or groups (selected from halogen, $C_{1-6}$alkyl, $C_{1-6}$alkoxy, or $C_{1-6}$alkoxy substituted by one or more fluorine atoms), or together with the nitrogen atom to which they are attached form a saturated 4 to 8 membered ring; and
pharmaceutically acceptable derivatives thereof.

Compounds of formula (I) are potent and selective inhibitors of COX-2 and are of use in the treatment of the pain, fever, inflammation of a variety of conditions and diseases.

35 Claims, No Drawings

PYRAZOLOPYRIDINES

CROSS-REFERENCES TO RELATED APPLICATIONS

This application is a Rule 371 Application of PCT Application No. EP99/10263, filed Dec. 22, 1999, which claims priority to GB Application Serial No. 9904506.4, filed Feb. 27, 1999 and GB Application Serial No. 9920904.1, filed Sep. 3, 1999.

This invention relates to pyrazolo[1,5-a]pyridine derivatives, to processes for their preparation, to pharmaceutical compositions containing them and to their use in medicine.

The enzyme cyclooxygenase (COX) has recently been discovered to exist in two isoforms, COX-1 and COX-2. COX-1 corresponds to the originally identified constitutive enzyme while COX-2 is rapidly and readily inducible by a number of agents including mitogens, endotoxin, hormones, cytokines and growth factors. Prostaglandins generated by the action of COX have both physiological and pathological roles. It is generally believed that COX-1 is responsible for the important physiological functions such as maintenance of gastrointestinal integrity and renal blood flow. In contrast the inducible form, COX-2, is believed to be responsible for the pathological effects of prostaglandins where rapid induction of the enzyme occurs in response to such agents as inflammatory agents, hormones, growth factors and cytokines. A selective inhibitor of COX-2 would therefore have anti-inflammatory, anti-pyretic and analgesic properties, without the potential side effects associated with inhibition of COX-1. We have now found a novel group of compounds which are both potent and selective inhibitors of COX-2.

DETAILED DESCRIPTION OF THE INVENTION

The invention thus provides the compounds of formula (I)

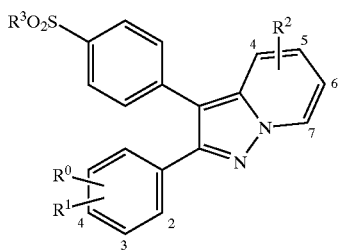

(I)

and pharmaceutically acceptable derivatives thereof in which:

$R^0$ and $R^1$ are independently selected from H, halogen, $C_{1-6}$alkyl, $C_{1-6}$alkoxy, or $C_{1-6}$alkoxy substituted by one or more fluorine atoms;

$R^2$ is halogen, CN, $CONR^4R^5$, $CO_2H$, $CO_2C_{1-6}$alkyl, or $NHSO_2R^4$;

$R^3$ is $C_{1-6}$alkyl or $NH_2$; and $R^4$ and $R^5$ are independently selected from H, $C_{1-6}$alkyl, phenyl, phenyl substituted by one or more atoms or groups (selected from halogen, $C_{1-6}$alkyl, $C_{1-6}$alkoxy, or $C_{1-6}$alkoxy substituted by one or more fluorine atoms), or together with the nitrogen atom to which they are attached form a saturated 4 to 8 membered ring.

By pharmaceutically acceptable derivative is meant any pharmaceutically acceptable salt, solvate or ester, or salt or solvate of such ester, of the compounds of formula (I), or any other compound which upon administration to the recipient is capable of providing (directly or indirectly) a compound of formula (I) or an active metabolite or residue thereof.

It will be appreciated by those skilled in the art that the compounds of formula (I) may be modified to provide pharmaceutically acceptable derivatives thereof at any of the functional groups in the compounds. Of particular interest as such derivatives are compounds modified at the benzenesulphonamide function to provide metabolically labile benzenesulphonamides.

Acylated benzenesulphonamide derivatives are of especial interest. Examples of such benzenesulphonamide derivatives include:

N-alkylcarbonylbenzenesulphonamides;
N-alkoxyalkylcarbonylbenzenesulphonamides;
N-alkoxycarbonylbenzenesulphonamides;
N-arylcarbonylbenzenesulphonamides;
N-alkoxycarbonylalkylcarbonylbenzenesulphonamides;
N-carboxylalkylcarbonylbenzenesulphonamides;
N-alkylcarbonyloxyalkylcarbonylbenzenesulphonamides;
N-alkylaminoalkylcarbonylbenzenesulphonamides; and
N-dialkylaminoalkylcarbonylbenzenesulphonamides.

With reference to such benzenesulphonamide derivatives, and by way of example only, alkyl may be $C_{1-6}$alkyl or $C_{1-6}$alkyl substituted by one or more halogen (e.g. chlorine) atoms; alkoxy may be $C_{1-6}$alkoxy or $C_{1-6}$alkoxy substituted by one or more halogen (e.g. chlorine) atoms; and aryl may be phenyl or substituted phenyl.

It will be appreciated by those skilled in the art that the pharmaceutically acceptable derivatives of the compounds of formula (I) may be derivatised at more than one position.

It will be further appreciated by those skilled in the art that benzenesulphonamide derivatives of formula (I) may be useful as intermediates in the preparation of compounds of formula (I), or as pharmaceutically acceptable derivatives of formula (I), or both.

It will be appreciated that, for pharmaceutical use, the salts referred to above will be the physiologically acceptable salts, but other salts may find use, for example in the preparation of compounds of formula (I) and the physiologically acceptable salts thereof.

Suitable pharmaceutically acceptable salts of the compounds of formula (I) include acid addition salts formed with inorganic or organic acids, preferably inorganic acids, e.g. hydrochlorides, hydrobromides and sulphates.

The term halogen is used to represent fluorine, chlorine, bromine or iodine.

The term 'alkyl' as a group or part of a group means a straight or branched chain alkyl group, for example a methyl, ethyl, n-propyl, i-propyl, n-butyl, s-butyl or t-butyl group.

In one aspect of the invention $R^0$ is at the 3- or 4-position of the phenyl ring, as defined in formula (I).

In another aspect of the invention $R^2$ is at the 6-position of the pyrazolopyridine ring, as defined in formula (I).

In another aspect of the invention $R^0$ and $R^1$ are independently H, halogen or $C_{1-4}$alkoxy.

In another aspect of the invention $R^2$ is CN or halogen.

In another aspect of the invention $R^3$ is $C_{1-3}$alkyl or $NH_2$.

Within the invention there is provided one group of compounds of formula (I) (group A) wherein: $R^0$ and $R^1$ are independently H, halogen or $C_{1-4}$alkoxy; $R^2$ is CN or halogen; and $R^3$ is $C_{1-3}$alkyl or $NH_2$.

Within group A, there is provided a further group of compounds (group A1) wherein: $R^0$ is F; $R^1$ is H; $R^2$ is CN or Br; and $R^3$ is methyl or $NH_2$.

Within group A, there is provided a further group of compounds (group A2) wherein: $R^0$ is F; $R^1$ is H; $R^2$ is CN, Br or Cl; and $R^3$ is methyl or $NH_2$.

Within groups A, A1 and A2 there are provided further groups of compounds wherein $R^0$ is at the 3- or 4-position (preferably the 4-position) of the phenyl ring and $R^2$ is at the 6-position of the pyrazolopyridine ring, as defined in formula (I).

It is to be understood that the present invention encompasses all isomers of the compounds of formula (I) and their pharmaceutically acceptable derivatives, including all geometric, tautomeric and optical forms, and mixtures thereof (e.g. racemic mixtures).

In one aspect the invention provides the compounds:
4-[6-cyano-2-(4-fluorophenyl)pyrazolo[1,5-a]pyridin-3-yl]benzenesulfonamide;
2-(4-fluorophenyl)-3-[4-(methylsulfonyl)phenyl]pyrazolo[1,5-a]pyridine-6-carbonitrile;
4-[6-bromo-2-(4-fluorophenyl)pyrazolo[1,5-a]pyridin-3-yl]benzenesulfonamide;
6-bromo-2-(4-fluorophenyl)-3-[4-(methylsulfonyl)phenyl]pyrazolo[1,5-a]pyridine;
and pharmaceutically acceptable derivatives thereof.

In another aspect the invention provides the compounds:
4-[6-chloro-2-(4-fluorophenyl)pyrazolo[1,5-a]pyridin-3-yl]benzenesulfonamide;
4-[6-chloro-2-(4-ethoxyphenyl)pyrazolo[1,5-a]pyridin-3-yl]benzenesulfonamide;
4-[6-chloro-2-(3-fluorophenyl)pyrazolo[1,5-a]pyridin-3-yl]benzenesulfonamide;
4-[6-chloro-2-phenyl-pyrazolo[1,5-a]pyridin-3-yl]benzenesulfonamide;
and pharmaceutically acceptable derivatives thereof.

Compounds of the invention are potent and selective inhibitors of COX-2. This activity is illustrated by their ability to selectively inhibit COX-2 over COX-1.

In view of their selective COX-2 inhibitory activity, the compounds of the present invention are of interest for use in human and veterinary medicine, particularly in the treatment of the pain (both chronic and acute), fever and inflammation of a variety of conditions and diseases mediated by selective inhibition of COX-2. Such conditions and diseases are well known in the art and include rheumatic fever; symptoms associated with influenza or other viral infections, such as the common cold; lower back and neck pain; headache; toothache; sprains and strains; myositis; neuropathic pain (e.g. neuralgia, such as post herpetic neuralgia, trigeminal neuralgia and sympathetically maintained pain); synovitis; arthritis, including rheumatoid arthritis; degenerative joint diseases, including osteoarthritis; gout and ankylosing spondylitis; tendinitis; bursitis; skin related conditions, such as psoriasis, eczema, bums and dermatitis; injuries, such as sports injuries and those arising from surgical and dental procedures.

The compounds of the invention are also useful for the treatment of other conditions mediated by selective inhibition of COX-2.

For example, the compounds of the invention inhibit cellular and neoplastic transformation and metastatic tumour growth and hence are useful in the treatment of certain cancerous diseases, such as colonic cancer.

Compounds of the invention also prevent neuronal injury by inhibiting the generation of neuronal free radicals (and hence oxidative stress) and therefore are of use in the treatment of stroke; epilepsy; and epileptic seizures (including grand mal, petit mal, myoclonic epilepsy and partial seizures).

Compounds of the invention also inhibit prostanoid-induced smooth muscle contraction and hence are of use in the treatment of dysmenorrhoea and premature labour.

Compounds of the invention inhibit inflammatory processes and therefore are of use in the treatment of asthma, allergic rhinitis and respiratory distress syndrome; gastrointestinal conditions such as inflammatory bowel disease, Chron's disease, gastritis, irritable bowel syndrome and ulcerative colitis; and the inflammation in such disease s as vascular disease, migraine, periarteritis nodosa, thyroiditis, aplastic anemia, Hodgkin's disease, sclerodoma, type I diabetes, myasthenia gravis, multiple sclerosis, sorcoidosis, nephrotic syndrome, Bechet's syndrome, polymyositis, gingivitis, conjunctivitis and myocardial ischemia.

Compounds of the invention are also useful in the treatment of ophthalmic diseases such as retinitis, retinopathies, uveitis and of acute injury to the eye tissue.

Compounds of the invention are also useful for the treatment of cognitive disorders such as dementia, particularly degenerative dementia (including senile dementia, Alzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Impairment.

According to a further aspect of the invention, we provide a compound of formula (I) or a pharmaceutically acceptable derivative thereof for use in human or veterinary medicine.

According to another aspect of the invention, we provide a compound of formula (I) or a pharmaceutically acceptable derivative thereof for use in the treatment of a condition which is mediated by selective inhibition of COX-2.

According to a further aspect of the invention, we provide a method of treating a human or animal subject suffering from a condition which is mediated by selective inhibition of COX-2 which comprises administering to said subject an effective amount of a compound of formula (I) or a pharmaceutically acceptable derivative.

According to a further aspect of the invention, we provide a method of treating a human or animal subject suffering from an inflammatory disorder, which method comprises administering to said subject an effective amount of a compound of formula (I) or a pharmaceutically acceptable derivative thereof.

According to another aspect of the invention, we provide the use of a compound of formula (1) or a pharmaceutically acceptable derivative thereof for the manufacture of a therapeutic agent for the treatment of a condition which is mediated by selective inhibition of COX-2.

According to another aspect of the invention, we provide the use of a compound of formula (I) or a pharmaceutically acceptable derivative thereof for the manufacture of a therapeutic agent for the treatment of an inflammatory disorder.

It is to be understood that reference to treatment includes both treatment of established symptoms and prophylactic treatment, unless explicitly stated otherwise.

It will be appreciated that the compounds of the invention may advantageously be used in conjunction with one or more other therapeutic agents. Examples of suitable agents for adjunctive therapy include pain relievers such as a glycine antagonist, a sodium channel inhibitor (e.g. lamotrigine), a substance P antagonist (e.g. an $NK_1$ antagonist), acetaminophen or phenacetin; a matrix metalloproteinase inhibitor; a nitric oxide synthase (NOS) inhibitor (e.g. an iNOS or an nNOS inhibitor); an inhibitor of the release, or action, of tumour necrosis factor α; an antibody therapy (e.g. a monoclonal antibody therapy); a stimulant, including caffeine; an $H_2$-antagonist, such as ranitidine; a proton pump inhibitor, such as omeprazole; an antacid, such as aluminium or magnesium hydroxide; an antiflatulent, such as simethicone; a decongestant, such as phenylephrine, phenylpropanolamine, pseudoephedrine, oxymetazoline, epinephrine, naphazoline, xylometazoline, propylhexedrine, or levo-desoxyephedrine; an antitussive, such as codeine, hydrocodone, carmiphen, carbetapentane, or dextramethorphan; a diuretic; or a sedating or non-sedating antihistamine. It is to be understood that the present invention covers the use of a compound of formula (I) or a pharmaceutically acceptable derivative thereof in combination with one or more other therapeutic agents.

The compounds of formula (I) and their pharmaceutically acceptable derivatives are conveniently administered in the form of pharmaceutical compositions. Thus, in another aspect of the invention, we provide a pharmaceutical composition comprising a compound of formula (I) or a pharmaceutically acceptable derivative thereof adapted for use in human or veterinary medicine. Such compositions may conveniently be presented for use in conventional manner in admixture with one or more physiologically acceptable carriers or excipients.

The compounds of formula (I) and their pharmaceutically acceptable derivatives may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable derivatives.

For oral administration, the pharmaceutical composition may take the form of, for example, tablets (including sublingual tablets), capsules, powders, solutions, syrups or suspensions prepared by conventional means with acceptable excipients.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

As stated above, the compounds of the invention may also be used in combination with other therapeutic agents. The invention thus provides, in a further aspect, a combination comprising a compound of formula (I) or a pharmaceutically acceptable derivative thereof together with a further therapeutic agent.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A proposed daily dosage of a compound of formula (I) for the treatment of man is 0.01 mg/kg to 500 mg/kg, such as 0.05 mg/kg to 100 mg/kg, e.g. 0.1 mg/kg to 50 mg/kg, which may be conveniently administered in 1 to 4 doses. The precise dose employed will depend on the age and condition of the patient and on the route of administration. Thus, for example, a daily dose of 0.25 mg/kg to 10 mg/kg may be suitable for systemic administration.

Compounds of formula (I) and pharmaceutically acceptable derivatives thereof may be prepared by any method known in the art for the preparation of compounds of analogous structure.

Suitable methods for the preparation of compounds of formula (I) and pharmaceutically acceptable derivatives thereof are described below. In the discussion and formulae that follow $R^0$ to $R^3$ are as defined in formula (I) above unless otherwise stated; Hal is a halogen, such as Br or I; $X^-$ is a counterion, such as $I^-$; NBS is N-bromosuccinimide; NCS is N-chlorosuccinimide; DMF is N,N-dimethylformamide; Me is methyl; unsubstituted derivatives of formulae (II), (IV) and (VII) are ones where $R^2$ is replaced by H; and alkyl and halogen are as previously defined.

Thus according to a first process (A), compounds of formula (I) may be prepared by reacting a compound of formula (II)

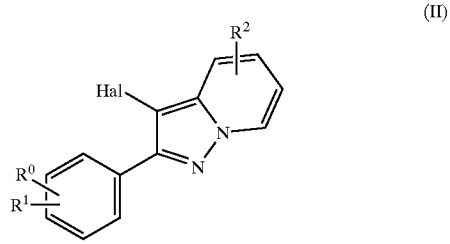

(II)

with a boronic acid of formula (III)

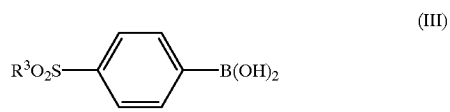

(III)

or a suitable derivative thereof in the presence of a suitable transition metal catalyst. Conveniently, the reaction is carried out in a solvent, such as an ether (e.g. 1,2 dimethoxyethane); in the presence of a base, such as an inorganic base (e.g. sodium carbonate); and employing a palladium catalyst, such as tetrakis(triphenylphosphine)palladium(0).

According to a another process (B), compounds of formula (I) wherein $R^3$ is $C_{1-6}$alkyl may be prepared by oxidising a compound of formula (IV)

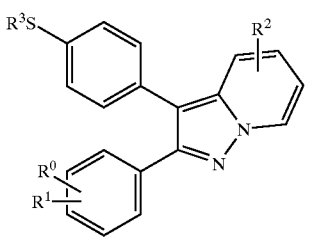
(IV)

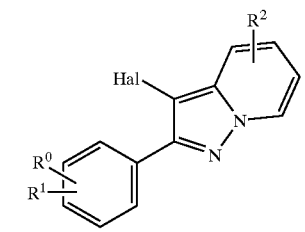
(II)

Thus according to another process (E), compounds of formula (I) may be prepared by reacting a compound of formula (II)

with a stanane of formula (XVII)

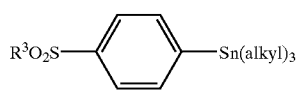
(XVII)

under conventional conditions. Conveniently the oxidation is effected using a monopersulfate compound, such as potassium peroxymonosulfate (known as Oxone™) and the reaction is carried out in a solvent, such as an aqueous alcohol, (e.g. aqueous methanol), and at between −78° C. and ambient temperature.

According to a another process (C), compounds of formula (I) wherein $R^2$ is halogen may be prepared by halogenating a compound of formula (V)

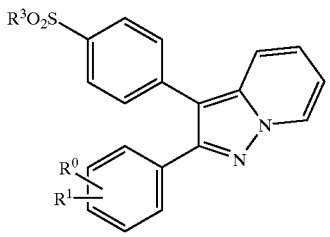
(V)

or a suitable derivative thereof in the presence of a suitable transition metal catalyst. Conveniently, the reaction is carried out in a solvent, such as an ether (e.g. dioxan); in the presence of a promoter, such as a halophilic metal oxide (e.g. silver oxide); at elevated temperature (e.g. under reflux); and employing a palladium catalyst, such as bis(diphenylphosphino)butane palladium(II) dichloride.

According to a another process (F), compounds of formula (I) wherein $R^3$ is $NH_2$ may be prepared by reacting a compound of formula (XVIII)

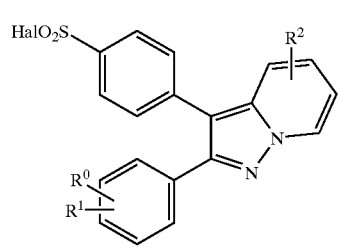
(XVIII)

under conventional conditions. Conveniently the halogenation is effected using halogen (e.g. bromine) or a suitable source of halogen (e.g. NBS or NCS); in the presence of a solvent, such as a halogenated alkane (e.g. trichloromethane); and at elevated temperature (e.g. under reflux).

According to a another process (D), compounds of formula (I) may be prepared by reacting a compound of formula (VI)

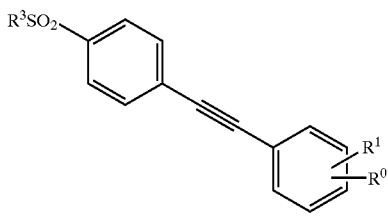
(VI)

with an aminopyridinium complex of formula (VII)

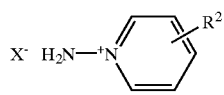
(VII)

under conventional conditions. Conveniently the reaction is effected in the presence of a base, such as an inorganic base (e.g. sodium carbonate); a solvent, such as a polar solvent (e.g. DMF); and at ambient or elevated temperature (e.g. ambient temperature).

with a source of ammonia under conventional conditions. Conveniently the reaction is carried out in a solvent, such as an ester (e.g. ethyl acetate); at ambient or elevated temperature (e.g. ambient temperature); employing ammonium hydroxide as the source of ammonia and using a compound of formula (XVIII) where Hal is Cl.

According to another process (G) compounds of formula (I) may be prepared by interconversion, utilising other compounds of formula (I) as precursors.

Suitable interconversions include, for example, conversion of: a cyano derivative to an amide derivative; an amide derivative to a cyano derivative; a carboxylic acid derivative to an amide derivative; an amide derivative to a carboxylic acid derivative; a carboxylic acid derivative to an ester derivative; and a carboxylic ester derivative to a carboxylic acid derivative.

The above interconversions may be carried out by conventional chemistry described in many standard texts on organic chemistry; see, for example, 'Advanced Organic Chemistry' by Jerry March, fourth edition (Wiley, 1992).

As will be appreciated by those skilled in the art it may be necessary or desirable at any stage in the synthesis of compounds of formula (I) to protect one or more sensitive groups in the molecule so as to prevent undesirable side reactions.

Another process (H) for preparing compounds of formula (I) thus comprises deprotecting protected derivatives of compounds of formula (I).

The protecting groups used in the preparation of compounds of formula (I) may be used in conventional manner. See, for example, those described in the standard reference text 'Protective Groups in Organic Synthesis' by Theodora W. Green and Peter G M Wuts, second edition, (John Wiley and Sons, 1991), incorporated herein by reference, which also describes methods for the removal of such groups.

Acylation of compounds of formula (I) wherein $R^3$ is $NH_2$ to provide corresponding acylated benzenesulphonamide derivatives may be carried out by conventional means, for example by employing conventional acylating agents such as those described in 'Advanced Organic Chemistry' by J March, fourth edition, (John Wiley and Sons, 1992), pp 417–424, incorporated herein by reference.

Compounds of formulae (II), (IV), (V) and (VI) may be prepared by any method known in the art for the preparation of compounds of analogous structure.

Compounds of formula (II) may, for example, be prepared according to Scheme 1 that follows.

In a variation of this scheme compounds of formula (IX) may be converted to the corresponding azirine by treatment with a base (e.g.) triethylamine, followed by cooling to about 0° C. and treatment with an anhydride (e.g. trifluoroactic anhydride). The azirine is then converted to the corresponding compound of formula (VIII) by dissolving the azirine in a solvent such as an aromatic hydrocarbon (e.g. 1,2,4-trichlorobenzene) and heating the solution (e.g. under reflux).

formula (II) may be prepared according to Scheme 1 by using 2-methylpyridine.

Compounds of formula (IV) may, for example, be prepared by reacting a compound of formula (II) with a boronic acid of formula (XIII)

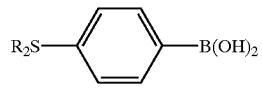

(XIII)

or a suitable derivative thereof under the conditions described above for the preparation of compounds of formula (I) according to process (A).

Compounds of formula (IV) wherein $R^2$ is halogen may also be prepared by halogenating unsubstituted derivatives of formula (IV) under the conditions described above for the preparation of compounds of formula (I) according to process (C). Unsubstituted derivatives of formula (IV) may be prepared by reacting the corresponding unsubstituted derivatives of formula (II) with a boronic acid of formula (XIII) under the conditions described above for the preparation of compounds of formula (I) according to process (A).

Compounds of formula (V) may, for example, be prepared by reacting an unsubstituted derivative of formula (II) with a boronic acid of formula (III) or a suitable derivative thereof under the conditions described above for the preparation of compounds of formula (I) according to process (A).

Scheme 1

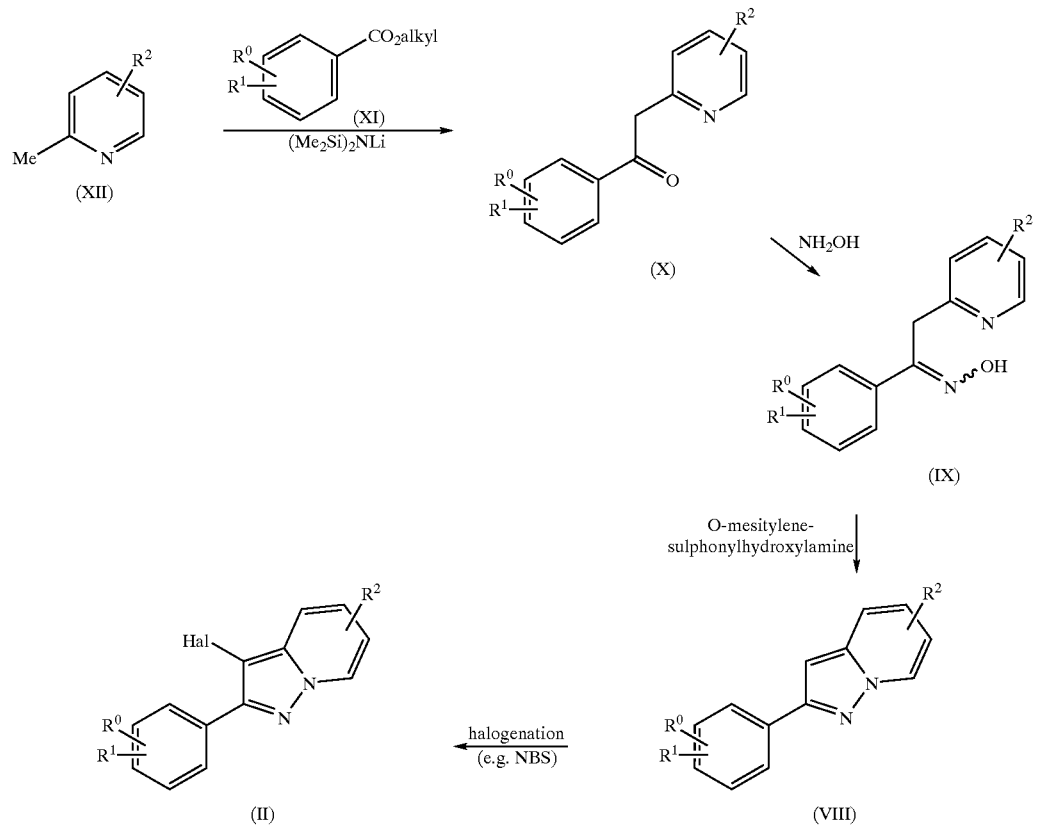

It will be appreciated by those skilled in the art that Scheme 1 may be adapted to provide unsubstituted derivatives of formula (II). Thus unsubstituted derivatives of Compounds of formula (V) may also be prepared under the conditions described above for the preparation of compounds of formula (I) according to process (D) by using an unsubstituted aminopyridinium derivative of formula (VII).

Compounds of formula (VI) may, for example, be prepared according to Scheme 2 that follows.

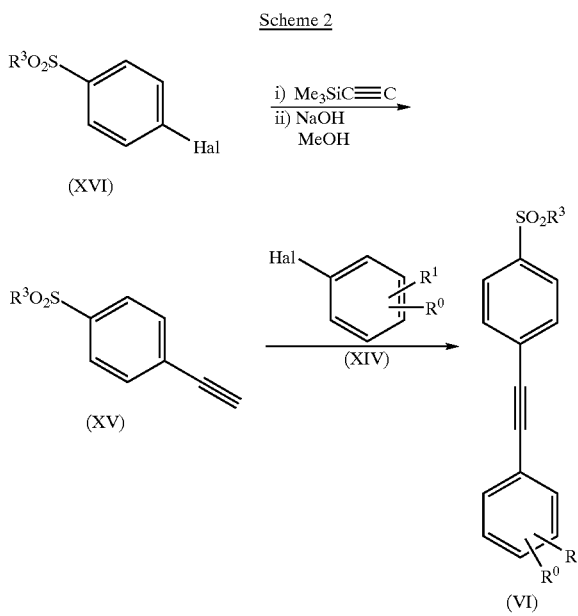

Scheme 2

The transformations illustrated in Schemes 1 and 2 may conveniently be carried out under conditions conventional for such reactions. The illustrated reaction conditions and reagents are by way of example.

It will be appreciated by those skilled in the art that it may be necessary or desirable to adapt schemes 1 or 2 to obtain certain compounds of formula (II), including unsubstituted derivatives thereof, and (VI).

Compounds of formula (II) wherein $R^2$ is CN are, for example, conveniently obtained according to Scheme 1 by reaction of the corresponding compound of formula (X) with O-mesitylene-sulphonylhydroxylamine to give the corresponding compound of formula (VIII).

Compounds of formula (XVIII) may be prepared by sulphonylating a compound of formula (XIX)

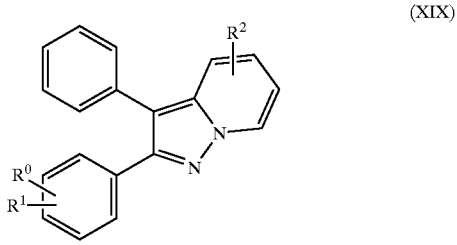

(XIX)

under conventional conditions. Conveniently the sulphonylation is effected using sulphonic acid or a derivative thereof, such as a halosulphonic acid (e.g. chlorosulphonic acid); in the presence of a solvent, such as a halogenated alkane (e.g. dichloromethane); and at between −78° C. and ambient temperature (e.g. −70° C.).

Boronic acids of formulae (III) and (XIII) are either known compounds or may be prepared by literature methods such as those described in, for example, EPA 533268. Suitable derivatives thereof include boronic acid esters, such as those described in R. Miyaura et al, J. Org. Chem., 1995, 60, 7508–7510, incorporated herein by reference.

Aminopyridinium complexes of formula (VII) and corresponding unsubstituted derivatives thereof are either known compounds or may be prepared by literature methods such as those described in, for example, Y Kobayashi et al, Chem Pharm Bull, (1971), 19(10), 2106–15; T. Tsuchiya, J. Kurita and K. Takayama, Chem. Pharm. Bull. 28(9) 2676–2681 (1980) and K Novitskii et al, Khim Geterotskil Soedin, 1970 2, 57–62, all incorporated herein by reference.

Compounds of formula (XI), (XII), (XIV) and (XVI) are either known compounds or may be prepared from known compounds by conventional chemistry.

Compounds of formula (XVII) may be prepared by literature methods such as those described in, for example, Mais, Dale E et al, J. Labelled Compd Radiopharm, (1991), 29(1), 75–9; and Azizian, Hormoz; Eaborn, Colin; Pidcock, Alan, J Organomet Chem, (1981), 215(1), 49–58.

Compounds of formula (XIX) may be prepared under the conditions described above for the preparation of the corresponding compounds of formula (I).

Certain intermediates described above are novel compounds, and it is to be understood that all novel intermediates herein form further aspects of the present invention. Compounds of formula (II), (IV), (V), (VI) and (XVIII) are key intermediates and represent a particular aspect of the present invention.

Conveniently, compounds of the invention are isolated following work-up in the form of the free base. Pharmaceutically acceptable acid addition salts of the compounds of the invention may be prepared using conventional means.

Solvates (e.g. hydrates) of a compound of the invention may be formed during the work-up procedure of one of the aforementioned process steps.

The following Examples illustrate the invention but do not limit the invention in any way. All temperatures are in ° C. Flash column chromatography was carried out using Merck 9385 silica. Biotage chromatography was carried out on a flash 40 i column (Biotage Limited). Solid Phase Extraction (SPE) chromatography was carried out using Varian Mega Bond Elut (Si) cartridges (Anachem) under 15 mmHg vacuum with stepped gradient elution. Thin layer chromatography (Tlc) was carried out on silica plates. NMR was carried out on a Brucker 400 MHz spectrometer. Chemical shifts are given, with respect to tetramethylsilane as internal chemical shift reference, in δ ppm. The following abbreviations are used: TFA, trifluoroacetic acid; THF, tetrahydrofuran; DCM, dichloromethane; NBS, N-bromosuccinimide; DMF, N,N-dimethylformamide; Me, methyl; s, singlet; d, doublet; t, triplet; and m, multiplet.

EXAMPLE 1

4-[6-Cyano-2-(4-fluorophenyl)pyrazolo[5-a]pyridin-3-yl]benzenesulfonamide i) 6-[2-(4-Fluorophenyl)-2-oxoethyl]nicotinonitrile To a solution of 3-cyano-6-methylpyridine (High Force Research Limited) (0.59 g 1,5 mmol) and ethyl 4-fluorobenzoate (0.84 g 5 mmol) (Aldrich) in dry THF (15 ml) stirring under nitrogen at −70° (Dricold/ethanol) was added dropwise lithium bis(trimethylsilyl)amide (10 ml M solution in hexane 10 mmol). The reaction was allowed to warm to room temperature, stirred under nitrogen for 20 hr, poured into water (200 ml) and extracted with ethyl acetate (3×50 ml). The combined extracts were washed with water (50 ml), brine (50 ml) and dried (MgSO$_4$). Removal of solvent gave a solid which was crystallised from ethanol to give the title compound as a yellow solid (0.74 g 62%) which existed as a mixture of keto- and enol-forms by NMR. MH$^+$: 241; mp: 170–1710 (uncorrected)

ii) 2-(4-Fluorophenyl)pyrazolo[1,5-a]pyridine-6-carbonitrile

Solid t-butoxycarbonyl-O-mesitylenesulfonylhydroxylamine (13.0 g 41.8 mmol)[1] was added portionwise with stirring to TFA (40 ml) over 10 min then stirred for a further 30 minutes. The solution was poured onto ice (250 ml) and left until the ice melted. The resulting white solid was filtered off, washed with water, and dissolved in DCM (300 ml). The solution was dried over 4 Å mol. sieves for 1.5 hours, filtered and 6-[2-(4-fluorophenyl)-2-oxoethyl]nicotinonitrile (3.32 g 13.8 mmol) was added. The reaction was stirred at room temperature for 4 days, washed with water (100 ml), dried and purified by column chromatography. Elution with cyclohexane/ethyl acetate (3:1) gave the title compound as a yellow solid (0.6 g 18%). NMR: (CDCl$_3$): δ 6.87 (1H, s) 7.15–7.20 (3H, m) 7.57 (1H, dd) 7.95 (2H, m) 8.84 (1H, d). Ref 1 Josef G Krause, Synthesis, 1972, 140.

iii) 3-Bromo-2-(4-fluorophenyl)pyrazolo[1,5-a]pyridine-6-carbonitrile

A solution of 2-(4-fluorophenyl)pyrazolo[1,5-a]pyridine-6-carbonitrile (0.6 g 2.53 mmol) and NBS (0.5 g 2.8 mmol) in DMF (10 ml) was stirred at room temperature for 2 hr. The reaction was poured into water (100 ml) and extracted with ethyl acetate (2×30 ml). The combined extracts were washed with water (30 ml), brine (30 ml), dried and purified by biotage chromatography. Elution with cyclohexane/ethyl acetate (20:1) gave the title compound as a white solid (0.483 g 61%). NMR: (CDCl$_3$): δ 7.21 (2H, t) 7.30 (1H, dd) 7.62 (1H, dd) 8.06 (2H, m) 8.80 (1H, s).

iv) 4-[6-Cyano-2-(4-fluorophenyl)pyrazolo[1,5-a]pyridin-3-yl]benzenesulfonamide

A mixture of 4-iodobenzenesulphonamide (0.5 g 1.1 mmol)[2]; dipinacoldiborane (0.456 g 1.1 mmol); potassium acetate (0.775 g 8 mmol); and [1,1'-bis(diphenylphosphino)-ferrocene]palladium(II) chloride complex:DCM (1:1) (0.04 g); in DMF (8 ml) was heated under nitrogen at 90° for 2 h. To the cooled reaction mixture was added 3-bromo-2-(3-fluoro-phenyl)-6-trifluoromethyl-pyrazolo[1,5-a]pyridine (0.231 g 0.73 mmol), 2N Na$_2$CO$_3$ (4 ml) and tetrakis (triphenylphosphine)-palladium (0) (0.04 g) and the mixture heated at 90° under nitrogen for 18 hours. The cooled reaction mixture was poured into water (100 ml) and the suspension extracted with ethyl acetate (3×30 ml). The combined extracts were washed with water (30 ml), brine (30 ml) and dried. Removal of solvent gave a brown solid which was purified by biotage chromatography. Elution with cyclohexane/ethyl acetate (2:1) gave the title compound as a white solid (0.151 g 65%). MH$^+$ 393; NMR: (CDCl$_3$): δ 4.87 (2H, br) 7.08 (2H, t) 7.28 (1H, dd) 7.48 (2H, d) 7.55 (2H, m) 7.60 (1H, d) 7.98 (2H, d) 8.89 (1H, d); Ref 2 Jaspal Singh and Paul Wyeth, J Enzyme Inhib., 1991, 5, 1.

EXAMPLE 2

2-(4-Fluorophenyl)-3-[4-(methylsulfonyl)phenyl] pyrazolo[1,5-a]pyridine-6-carbonitrile To a solution of 3-bromo-2-(4-fluorophenyl)pyrazolo[1,5-a]pyridine-6-carbonitrile (0.24 g 0.76 mmol) in DMF (20 ml) was added 4-methanesulfonylphenylboronic acid (0.202 g 1.1 mmol), ground potassium phosphate (0.45 g 20 mmol) and tetrakis(triphenylphosphine)palladium(0) (0.03 g) and the mixture heated to 90° for 6 h under nitrogen. The cooled mixture was poured into water (200 ml) and extracted with ethyl acetate (3×40 ml). The combined organic phases were washed with water (50 ml), brine (50 ml) and dried. Removal of solvent gave a solid which was purified by biotage chromatography. Elution with cyclohexane:ethyl acetate (4:1) gave the title compound as a white solid (0.019 g 6%). MH$^+$: 392; NMR: (CDCl$_3$) δ 3.14 (3H, s) 7.09 (2H, t) 7.30 (1H, dd) 7.50–7.56 (4H, m) 7.62 (1H, dd) 8.00 (2H, d) 8.9 (1H, s).

EXAMPLE 3

4-[6-Bromo-2-(4-fluorophenyl)pyrazolo[1,5-a] pyridin-3-yl]benzenesulfonamide i) 1-(4-Fluorophenyl)-2-pyridin-2-ylethanone By using 2-methylpyridine (4.65 g, 50 mmol) the title compound was obtained as a yellow solid (6.28 g 58%) in the manner described in Example 1(i). It existed as a mixture of keto- and enol-forms by NMR. MH$^+$: 216.

ii) 1-(4-Fluorophenyl)-2-pyridin-2-ylethanone Oxime

To a solution of 1-(4-fluorophenyl)-2-pyridin-2-ylethanone (6.27 g 29 mmol) in methanol (100 ml) was added a solution of hydroxylamine hydrochloride (9.6 g 130 mmol) and sodium acetate (15.6 g) in water (80 ml) and the reaction was stirred at room temperature for 24 hours. The resulting precipitate was filtered off and dried to give the title compound as a white solid (5.83 g 87%). (M-H$_2$O)H$^+$: 213; NMR: (CDCl$_3$): δ 4.42 (2H, s) 7.00 (2H, t) 7.14 (1H, m) 7.28 (1H, d) 7.59 (1H, dt) 7.72 (2H, m) 8.55 (1H, m) 8.96 (1H, br).

iii) 2-(4-Fluorophenyl)pyrazolo[1,5-a]pyridine

Solid t-butoxycarbonyl-O-mesitylenesulfonylhydroxylamine (17.26 54.6 mmol) was added portionwise with stirring to TFA (50 ml) over 10 min then stirred for a further 30 minutes. The solution was poured onto ice (~250 ml) and left until the ice melted. The resulting white solid was filtered off, washed with water, and dissolved in chloroform (200 ml). The solution was dried over 4 Å mol. sieves for 1.5 hours, filtered and 1-(4-fluorophenyl)-2-pyridin-2-ylethanone oxime (6.29 g 27.3 mmol) in chloroform (100 ml) was added. The reaction was stirred at room temperature for 18 hours, washed with water (2×50 ml) and dried. Removal of solvent gave a brown solid which was purified by biotage chromatography. Elution with cyclohexane/ethyl acetate (20/1) gave the title compound as a yellow solid (4.09 g 71%). MH$^+$: 213; NMR: (CDCl$_3$): δ 6.75 (2H, m) 7.10 (3H, m) 7.50 (1H, d) 7.95 (2H, m) 8.45 (1H, d).

iv) 3-Bromo-2-(4-fluorophenyl)pyrazolo[1,5-a]pyridine

By using (2-(4-fluorophenyl)pyrazolo[1,5-a]pyridine (4.08 g 19.3 mmol) the title compound was obtained as a white solid (5.46 g 97%) in the manner described in Example 1 (iii). MH$^+$: 291, 293; NMR: (CDCl$_3$): δ 6.80 (1H, t) 7.20 (3H, m) 7.55 (1H, d) 8.05 (2H, m) 8.45 (1H, d).

v) 4-[2-(4-Fluorophenyl)pyrazolo[1,5-a]pyridin-3-yl] benzenesulfonamide

By using 3-bromo-2-(4-fluorophenyl)pyrazolo[1,5-a] pyridine (0.87 g, 3 mmol) the title compound was obtained as a white solid (0.067 g 6%) in the manner described in Example 1(iv). MH$^+$: 368; NMR: (CDCL3): δ 4.87 (2H, br) 6.87 (1H, dt) 7.06 (2H, t) 7.23 (1H, m) 7.48–7.60 (5H, m) 7.95 (2H, d) 8.53 (1 H, d).

vi) 4-[6-Bromo-2-(4-fluorophenyl)pyrazolo[1,5-a]pyridin-3-yl]benzenesulfonamide

A mixture of 4-[2-(4-fluorophenyl)pyrazolo[1,5-a] pyridin-3-yl]benzenesulfonamide (0.062 g 0.17 mmol) and bromine (0.03 g 0.17 mmol) in chloroform (3 ml) was heated under reflux for 24 hours. The reaction mixture was diluted with chloroform (20 ml), washed with M sodium thiosulphate (10 ml), water (10 ml) and dried. Removal of solvent gave a brown solid which was purified by SPE chromatography. Elution with cyclohexane/ethyl acetate (10/1) gave the title compound as a white solid (0.025 g 32%). MH$^+$: 446, 448; NMR: (d6-acetone): δ 6.55 (2H, br) 7.05 (2H, t) 7.30 (1H, d) 7.45 (2H, d) 7.50 (2H, m) 7.55 (1H, d) 7.80 (2H, d) 8.80 (1H, s).

EXAMPLE 4

6-Bromo-2-(4-fluorophenyl)-3-[4-(methylsulfonyl)phenyl]pyrazolo[1,5-a]pyridine i) 2-(4-fluorophenyl)-3-[4-(methylsulfanyl)phenyl]pyrazolo[1,5-a]pyridine By using 3-bromo-2-(4-fluorophenyl)pyrazolo[1,5-a]pyridine (4.0 g, 13.8 mmol) and 4-methylsulphanylphenylboronic acid (3.07 g, 1.83 mmol) the title compound was obtained as a white solid (2.29 g 50%) in the manner described in Example 2. MH$^+$: 335; NMR: (CDCl$_3$) δ 2.53 (3H, s) 6.80 (1H, t) 7.00 (2H, t) 7.15 (1H, t) 7.25 (2H, d) 7.30 (1H, d) 7.50 (2H, d) 7.60 (2H, m) 8.50 (1H, d).

ii) 6-Bromo-2-(4-fluorophenyl)-3-[4-(methylsulfanyl)phenyl]pyrazolo[1,5-a]pyridine By using 2-(4-fluorophenyl)-3-[4-(methylsulfanyl)phenyl]pyrazolo[1,5-a]pyridine (0.664 g, 2 mmol) the title compound was obtained as a white solid (0.266 g 32%) in the manner described in Example 3(vi). MH$^+$: 413, 415; NMR: (CDCl$_3$): δ 2.54 (3H, s) 7.04 (2H, t) 7.18 (1H, dd) 7.33 (2H d) 7.41 (1H, d) 7.50 (2H, d) 7.57 (2H, m) 8.63 (1H, d).

iii) 6-Bromo-2-(4-fluorophenyl)-3-[4-(methylsulfonyl)phenyl]pyrazolo[1,5-a]pyridine To a solution of 6-bromo-2-(4-fluorophenyl)-3-[4-(methylsulfanyl)phenyl]pyrazolo[1,5-a]pyridine (0.26 g 0.63 mmol) in acetone (30 ml) was added a solution of oxone (1.16 g 1.9 mmol) in water (10 ml). The reaction was stirred at room temperature for 20 hours, further oxone (1 g 1.7 mmol) in water (10 ml) was added and stirring was continued for 6 hours. The reaction mixture was poured into water (200 ml) and extracted with ethyl acetate (3×30 ml). The combined extracts were washed with water (30 ml), brine (30 ml) and dried. Removal of solvent gave a solid which was purified by biotage chromatography. Elution with cyclohexane ethyl acetate gave the title compound as a white solid (0.13 g 58%). MH$^+$: 445, 447. NMR: (CDCl$_3$) δ 3.13 (3H, s) 7.07 (2H, t) 7.29 (1H, dd) 7.45–7.55 (5H, m) 7.96 (2H, d) 8.67 (1H, s).

EXAMPLE 5

4-[6-Chloro-2-(4-fluorophenyl)pyrazolo[1,5-a]pyridin-3-yl]benzenesulfonamide (i) 4-(Tri-n-butylstannyl)phenylsulfonamide A mixture of 4-iodophenyl sulfonamide (20 g, 70.65 mmol), hexabutylditin (50 g, 86.2 mmol) and tetrakis(triphenylphosphine)palladium (0) (500 mg) in toluene/dioxan (1:1, 350 ml) was heated at reflux under nitrogen for 48 h. On cooling, the reaction mixture was concentrated onto silica gel and purified by flash column chromatography (400 g) with cyclohexane:ethyl acetate (8:1 then 3:1) to give the title compound as a colourless oil (18.22 g, 58%). NMR (CDCl$_3$) δ 0.89 (9H, t); 1.1(6H, t); 1.33 (6H, m); 1.53 (6H, m); 4.80 (2H, s, NH2); 7.63 (2H, d, J 8 Hz, arom ); 7.85 (2H, d, J 8Hz, arom) Tlc SiO$_2$ cyclohexane: ethyl acetate (3:1) Rf 0.44 detection uv$_{254}$.

ii) 2-(5-Chloropyridin-2-yl)-1-(4-fluorophenyl)ethanone

Sodium hydride (Aldrich, 60% in oil, 13.03 g) was suspended in anhydrous THF (250 ml). 4-Fluoroacetophenone (15 g, 108.6 mmol) in anhydrous THF (100 ml) was added dropwise and the mixture heated to reflux for 1 h under nitrogen. The solution was cooled to 0° and 2,5 dichloropyridine (16.07 g) in anhydrous THF (75 ml) was added dropwise. The mixture was then heated to reflux overnight before being recooled to 0° and quenched with water dropwise (CAUTION! Hydrogen gas evolved, exothermic). The resulting reaction mixture was washed with brine and the organic phase dried and concentrated to give a mobile brown oil which was adsorbed onto silica gel and purified by Biotage chromatography with cyclohexane:ethyl acetate (40:1) as eluant. Combination and concentration of appropriate fractions gave the title compound as a yellow solid (2.31 g, 8.5%) which exists as a mixture of keto:enol forms, 1:2. NMR (CDCl$_3$) δ 4.44 (2H, s, keto CH2); 6.0 (apparent 2H, s, enol CH═); 7.05–7.15 (10H, m); 7.26 (1H, d, J 9 Hz); 7.6–7.65 (apparent 3H, 2x dd, J 9 & 2 Hz); 7.8 (4H, dd, J 9 & 5 Hz); 8.35 (apparent 2H, J 3 Hz, N═CH); 8.52 (1H, J 3 Hz, N═CH) Tlc SiO$_2$ cyclohexane: ethyl acetate (3:1) Rf 0.56 detection uv$_{254}$.

iii) 2-(5-Chloropyridin-2-yl)-1-(4-fluorophenyl)ethanone Oxime

Sodium acetate (6.47 g) and hydroxylamine hydrochloride (5.74 g) were dissolved in water (45 ml) and added to a solution of 2-(5-chloropyridin-2-yl)-1-(4-fluorophenyl)ethanone (3.39 g, 13.6 mmol) in methanol (200 ml). After heating at reflux for 2 h, the cooled reaction mixture was partitioned between water and ethyl acetate and the organic phase dried and concentrated to give the title compound as a yellow solid (3.56 g, 98%). NMR (CDCl$_3$) δ 4.35 (2H, s, CH$_2$); 7.02 (2H, t, 8 Hz, arom); 7.25 (1H, d, J 9 Hz, arom); 7.53 (1H, dd, J 9 & 2 Hz, arom); 7.71 (2H, m, arom); 8.12 (1 H, br s, OH); 8.48 (1H, s, 2 Hz, arom); Tlc SiO$_2$ cyclohexane:ethyl acetate (3:1) Rf 0.42 detection uv$_{254}$.

iv) 6-Chloro-2-(4-Fluorophenyl)pyrazolo[1,5-a]pyridine

Solid t-butoxycarbonyl-O-mesitylenesulfonylhydroxylamine (8.45 g 26.8 mmol) was added portionwise with stirring to TFA (100 ml) over 10 min then stirred for a further 30 minutes. The solution was poured onto ice (~250 ml) and left until the ice melted. The resulting white solid was filtered off, washed with water, and dissolved in chloroform (200 ml). The solution was dried over 4 Å mol. sieves for 1.5 hours, filtered and 2-(5-chloropyridin-2-yl)-1-(4-fluorophenyl)ethanone oxime (3.56 g 13.4 mmol) in chloroform (100 ml) was added. The reaction was stirred at room temperature for 18 hours, washed with water (2×50 ml) and dried. Removal of solvent gave a brown solid which was purified by Biotage chromatography. Elution with cyclohexanelethyl acetate (35/1) gave the title compound as a yellow solid (2.476 g 75%). NMR (CDCl$_3$) δ 6.76 (1H, s, H-3); 7.08 (1H, dd, J 9 & 2 Hz, H-5); 7.13 (2H, t, J 9 Hz, H-3'); 7.45 (1H, d, J 9 Hz, H-4); 7.9 (2H, dd, J 9 & 5 Hz, H-2'); 8.5 (1H, d, J 2 Hz, H-7);

v) 3-Bromo-6-chloro-2-(4-fluorophenyl)pyrazolo[1,5-a]pyridine

6-Chloro2-(4-fluorophenyl)pyrazolo[1,5-a]pyridine (2.48 g, 10.05 mmol) was dissolved in anhydrous DMF (160 ml) and treated with NBS (1.967 g) for 1 h. The reaction mixture was partitioned between ethyl acetate and water. The organic phase was separated, washed with water, dried and concentrated to give the title compound as a brown solid (2.827 g, 86%). (CDCl$_3$) δ 7.19 (3H, t, J 9 Hz, H-3'+H-5); 7.48 (1H, d, J 9 Hz, H4); 8.05(2H, m, H-2'); 8.49 (1H, br s, H-7); Tlc SiO$_2$ cyclohexane:ethyl acetate (3:1) Rf 0.74 detection uv$_{254}$.

vi) 4-[6-Chloro-2-(4-fluorophenyl)pyrazolo[1,5-a]pyridin-3-yl]benzenesulfonamide 3-Bromo-6-chloro-2-(4-fluorophenyl)pyrazolo[1,5-a]pyridine (397 mg, 1.22 mmol), 4-(tri-n-butylstannyl)phenylsulfonamide (1.09 g), bis(diphenylphosphino)butane palladium(II) dichloride (100 mg) and silver oxide (283 mg) were stirred in anhydrous dioxan (15 ml) at reflux for 24 h. After cooling, the concentrated reaction mixture was taken up in DCM and concentrated onto silica gel which was loaded onto an SPE column and eluted with cyclohexane-:ethyl acetate (8:1). This gave a white solid which was triturated with cyclohexane and filtered to give the title compound as a white solid (165 mg, 34%). MH$^+$ 400 1H NMR (DMSO) δ 7.27 (2H, t, J 8 Hz); 7.4 (3H, m); 7.52 (4H, m); 7.7 (1H, d, J 9 Hz); 7.87 (2H, d, J 8 Hz); 9.18 (1H, s); Tlc SiO$_2$ cyclohexane:ethyl acetate (3:1) Rf 0.12 detection uv$_{254}$.

EXAMPLE 6

4-[6-Chloro-2-(4-ethoxyphenyl)pyrazolo[1,5-a]pyridin-3-yl]benzenesulfonamide The process represented by Example 5(i)–(vi) was repeated, but substituting 4-ethoxyacetophenone for 4-fluoroacetophenone in step (ii). The title compound was obtained from 3-bromo-6-chloro-2-(4-ethoxyphenyl)pyrazolo[1,5-a]pyridine (429 mg, 1.22 mmol) in the manner described for Example 5(vi), as a white solid (109 mg, 21%). MH$^+$ 426; NMR (DMSO) δ 1.41 (3H, t, J 7 Hz, CH$_3$); 4.15 (2H, q, J 7 Hz, CH$_2$); 7.05 (1H, d, J 8 Hz); 7.46 (1H, d, J 9 Hz); 7.51 (4H, m); 7.61 (2H, d, J 8 Hz); 7.75 (1H, d, 9 Hz); 7.95 (2H, d, 8 Hz); 9.22 (1H, s); TLC SiO$_2$ cyclohexane:ethyl acetate (3:1) Rf 0.13 detection uv$_{254}$.

EXAMPLE 7

4-[6-Chloro-2-(3-fluorophenyl)pyrazolo[1,5-a]pyridin-3-yl]benzenesulfonamide The process represented by Example 5(i)–(vi) was repeated, but substituting 3-fluoroacetophenone for 4-fluoroacetophenone in step (ii). The title compound was obtained from 3-bromo-6-chloro-2-(3-fluorophenyl)pyrazolo[1,5-a]pyridine (250 mg, 1.22 mmol) in the manner described for Example 5(vi), as a white solid (108 mg, 35%). 1H NMR (DMSO) 7.25–7.31 (3H, m); 7.43 (4H, m); 7.54 (2H, d, J 9 Hz); 7.7 (1H, d, J 9 Hz); 7.88 (2H, d, 9 Hz); 9.2 (1 H, br s); TLC SiO$_2$ Cyclohexane:ethyl acetate (3:1) Rf 0.14 Detection uv$_{254}$.

EXAMPLE 8

4-[6-Chloro-2-phenyl-pyrazolo[1,5-a]pyridin-3-yl]benzenesulfonamide i) 5-Chloro-2-phenylethynylpyridine A mixture of 2,5 dichloropyridine (3.7 g, 25 mmol), phenylacetylene (3.02 ml, 1.1 eq), bis triphenylphosphine palladium dichloride (II) (Aldrich, 500 mg), copper (I) iodide (250 mg) and triethylamine (50 ml) was heated to reflux under N$_2$ for 18 h. The cooled reaction mixture was diluted with water, extracted with diethyl ether, dried and concentrated to a black oil which was partially purified by SPE Si chromatography with gradient elution cyclohexane:ethyl acetate (100:0 to 10:1) gave the title compound as a brown solid (1.94 g, 36%). MH$^+$ 213; 1H NMR (CDCl$_3$) δ 7.37 (3H, m); 7.48 (1H, d, J 8 Hz); 7.59 (2H, m); 7.67 (1H, dd, J 8 & 2 Hz); 8.57 (1H, d, J 2 Hz); TLC SiO$_2$ Cyclohexane: ethyl acetate (15:1) Rf 0.36.

ii) 3-Bromo-6-chloro-2-phenylpyrazolo[1,5-a]pyridine

Solid t-butoxycarbonyl-O-mesitylenesulfonylhydroxylamine (3.16 g 10 mmol) was added portionwise with stirring to TFA (25 ml) over 10 min then stirred for a further 30 minutes. The solution was poured onto ice (~250 ml) and left until the ice melted. The resulting white solid was filtered off, washed with water, and dissolved in chloroform (100 ml). The solution was dried over 4 Å mol. sieves for 1.5 hours, filtered, treated with 5-chloro-2-phenylethynylpyridine (1.94 g, 9 mmol) in chloroform (10 ml) added and stirred at ambient temperature overnight. After concentrating in vacuo, the resulting semi-solid was suspended in MeCN (30 ml), DBU (1.63 ml) added and stirred for 18 h. The mixture was concentrated and partitioned between ethyl acetate and water. The combined organic phases were dried and concentrated to a brown solid which was partially purified by SPE chromatography with cyclohexane:ethyl acetate (50:1) to give an approximately 2:3 mixture of starting acetylene and desired cyclisation product (636 mg) (TLC SiO$_2$ cyclohexane:ethyl acetate (3:1) Rf 0.66), which was taken up in DMF (10 ml) cooled to 0° and treated with NBS (540 mg) and allowed to warm to room temperature, stirred for 2 h then poured into water and extracted into ethyl acetate (2×30 ml). The resulting light brown solid was purified by SPE Si chromatography with cyclohexane:ethyl acetate (50:1) as eluant to give a light brown solid (565 mg). A portion of this material (100 mg) was purified by HPLC with an acetonitrile:water gradient elution to give pure title compound (40 mg). MH$^+$ 308/309. Tlc SiO$_2$ (cyclohexane:ethyl acetate 3:1) Rf 0.77; NMR CDCl$_3$ δ 8.02 (1H, d, J 7 Hz); 7.5 (4H, m); 8.1 (2H, dd, J 7 & 2 Hz); 8.5 (1H, s).

iii) 4-[6-Chloro2-phenyl-pyrazolo[1,5-a]pyridin-3-yl]benzenesulfonamide

By using impure 3-bromo-6-chloro-2-(phenyl)pyrazolo[1,5-a]pyridine (300 mg, 1.22 mmol) the title compound was obtained as a white solid (52 mg, 14%) in the manner described in Example 5(vi). MH$^+$ 384; 1H NMR (CDCl$_3$) δ 4.85 (2H, br s); 7.19 (1H, dd, J 10 & 2 Hz); 7.38 (3H, m); 7.5 (3H, d, J 8 Hz); 7.52 (2H, m); 7.92 (2H, d, J 8 Hz); 8.58 (1H, m); TLC SiO$_2$ cyclohexane:ethyl acetate (3:1) Rf 0.66 Detection uv$_{254}$.

EXAMPLE 9

Tablets

| a) | | |
|---|---|---|
| | Compound of the invention | 5.0 mg |
| | Lactose | 95.0 mg |
| | Microcrystalline Cellulose | 90.0 mg |
| | Cross-linked polyvinylpyrrolidone | 8.0 mg |
| | Magnesium Stearate | 2.0 mg |
| | Compression weight | 200.0 mg |

The compound of the invention, microcrystalline cellulose, lactose and cross-linked polyvinylpyrrolidone are sieved through a 500 micron sieve and blended in a suitable mixer. The magnesium stearate is sieved through a 250 micron sieve and blended with the active blend. The blend is compressed into tablets using suitable punches.

| b) | | |
|---|---|---|
| | Compound of the invention | 5.0 mg |
| | Lactose | 165.0 mg |
| | Pregelatinised Starch | 20.0 mg |
| | Cross-linked polyvinylpyrrolidone | 8.0 mg |
| | Magnesium Stearate | 2.0 mg |
| | Compression weight | 200.0 mg |

The compound of the invention, lactose and pregelatinised starch are blended together and granulated with water. The wet mass is dried and milled. The magnesium stearate and cross-linked polyvinylpyrrolidone are screened through a 250 micron sieve and blended with the granule. The resultant blend is compressed using suitable tablet punches.

EXAMPLE 10

Capsules

| a) | Compound of the invention | 5.0 mg |
|---|---|---|
|  | Lactose | 193.0 mg |
|  | Magnesium Stearate | 2.0 mg |
|  | Fill weight | 200.0 mg |

The compound of the invention and pregelatinised starch are screened through a 500 micron mesh sieve, blended together and lubricated with magnesium stearate, (meshed through a 250 micron sieve). The blend is filled into hard gelatine capsules of a suitable size.

| b) | Compound of the invention | 5.0 mg |
|---|---|---|
|  | Lactose | 177.0 mg |
|  | Polyvinylpyrrolidone | 8.0 mg |
|  | Cross-linked polyvinylpyrrolidone | 8.0 mg |
|  | Magnesium Stearate | 2.0 mg |
|  | Fill weight | 200.0 mg |

The compound of the invention and lactose are blended together and granulated with a solution of polyvinylpyrrolidone. The wet mass is dried and milled. The magnesium stearate and cross-linked polyvinylpyrrolidone are screened through a 250 micron sieve and blended with the granules. The resultant blend is filled into hard gelatine capsules of a suitable size.

EXAMPLE 11

Syrup

| a) | Compound of the invention | 5.0 mg |
|---|---|---|
|  | Hydroxypropyl Methylcellulose | 45.0 mg |
|  | Propyl Hydroxybenzoate | 1.5 mg |
|  | Butyl Hydroxybenzoate | 0.75 mg |
|  | Saccharin Sodium | 5.0 mg |
|  | Sorbitol Solution | 1.0 ml |
|  | Suitable Buffers | qs |
|  | Suitable flavours | qs |
|  | Purified Water to | 10.0 ml |

The hydroxypropyl methylcellulose is dispersed in a portion of hot purified water together with the hydroxybenzoates and the solution is allowed to cool to ambient temperature. The saccharin, sodium flavours and sorbitol solution are added to the bulk solution. The compound of the invention is dissolved in a portion of the remaining water and added to the bulk solution. Suitable buffers may be added to control the pH in the region of maximum stability. The solution is made up to volume, filtered and filled into suitable containers.

EXAMPLE 12

Injection Formulation

|  | % w/v |
|---|---|
| Compound of the invention | 1.00 |
| Water for injections B.P. to | 100.00 |

Sodium chloride may be added to adjust the tonicity of the solution and the pH may be adjusted to that of maximum stability and/or to facilitate solution of the compound of the invention using dilute acid or alkali or by the addition of suitable buffer salts. Solubilisers, such as cosolvents, may also be added to facilitate solution of the compound of the invention. Antioxidants and metal chelating salts may also be included. The solution is clarified, made up to final volume with water and the pH remeasured and adjusted if necessary, to provide 10 mg/ml of the compound of formula (I).

The solution may be packaged for injection, for example by filling and sealing in ampoules, vials or syringes. The ampoules, vials or syringes may be aseptically filled (e.g. the solution may be sterilised by filtration and filled into sterile ampoules under aseptic conditions) and/or terminally sterilised (e.g. by heating in an autoclave using one of the acceptable cycles). The solution may be packed under an inert atmosphere of nitrogen.

Preferably the solution is filled into ampoules, sealed by fusion of the glass and terminally sterilised.

Further sterile formulations are prepared in a similar manner containing 0.5, 2.0 and 5% w/v of the compound of the invention, so as to provide respectively 5, 20 and 50 mg/ml of the compound of the invention.

Biological Data

Inhibitory activity against human COX-1 and COX-2 was assessed in COS cells which had been stably transfected with cDNA for human COX-1 and human COX-2. 24 Hours prior to experiment, COS cells were transferred from the 175 cm$^2$ flasks in which they were grown, onto 24-well cell culture plates using the following procedure. The incubation medium (Dulbecco's modified eagles medium (DMEM) supplemented with heat-inactivated foetal calf serum (10% v/v), penicillin (100 IU/ml), streptomycin (100$\mu$g/ml) and geneticin (600 $\mu$g/ml)) was removed from a flask of confluent cells (1 flask at confluency contains approximately 1×10$^7$ cells). 10 ml of phosphate buffered saline (PBS) was added to the flask to wash the cells. Having discarded the PBS, cells were then rinsed in 10 ml trypsin for 20 seconds, after which the trypsin was removed and the flask placed in an incubator (37°) for 1–2 minutes until cells became detached from the flask. The flask was then removed from the incubator and cells resuspended in 10 ml of fresh incubation medium. The contents of the flask was transferred to a 250 ml sterile container and the volume of incubation medium subsequently made up to 100 ml. 1 ml cell suspension was pipetted into each well of 4×24-well cell culture plates. The plates were then placed in an incubator (37° C., 95% air/5% CO$_2$) overnight. If more than 1 flask of cells were required, the cells from the individual flasks were combined before being dispensed into the 24-well plates.

Following the overnight incubation, the incubation medium was completely removed from the 24-well cell culture plates and replaced with 250 $\mu$l fresh DMEM (37° C.). The test compounds were made up to 250× the required test concentration in DMSO and were added to the wells in a volume of 1 μl. Plates were then mixed gently by swirling and then placed in an incubator for 1 hour (37° C., 95% air/5% $CO_2$). Following the incubation period, 10 μl of arachidonic acid (750 μM) was added to each well to give a final arachidonic acid concentration of 30 μM. Plates were then incubated for a further 15 minutes, after which the incubation medium was removed from each well of the plates and stored at −20° C., prior to determination of prostaglandin $E_2$ (PGE2) levels using enzyme immunoassay. The inhibitory potency of the test compound was expressed as an $IC_{50}$ value, which is defined as the concentration of the compound required to inhibit the PGE2 release from the cells by 50%. The selectivity ratio of inhibition of COX-1 versus COX-2 was calculated by comparing respective $IC_{50}$ values. The following $IC_{50}$ values for inhibition of COX-2 and COX-1 were obtained for compounds of the invention:

| Example No. | COX-2: $IC_{50}$(nM) | COX-1: $IC_{50}$(nM) |
|---|---|---|
| 1(iv) | 21 | 20,950 |
| 2 | 12 | >100,000 |
| 3(vi) | 1 | 6,765 |
| 4(iii) | 5 | >100,000 |
| 5(vi) | 21 | 20,950 |
| 6 | 12 | >100,000 |
| 7 | 1 | 6,765 |
| 8(iii) | 5 | >100,000 |

What is claimed is:

1. A compound of formula (I)

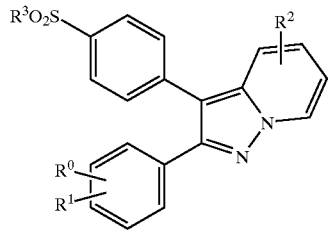

(I)

wherein
  $R^0$ and $R^1$ are independently selected from the group consisting of H, halogen, $C_{1-6}$alkyl, $C_{1-6}$alkoxy, and $C_{1-6}$alkoxy substituted by one or more fluorine atoms;
  $R^2$ is halogen, CN, $CONR^{45}$, $CO_2H$, $CO_2C_{1-6}$alkyl, or $NHSO_2R^4$;
  $R^3$ is $C_{1-6}$alkyl or $NH_2$; and
  $R^4$ and $R^5$ are independently selected from the group consisting of H, $C_{1-6}$alkyl, phenyl, phenyl substituted by one or more atoms or groups selected from the group consisting of halogen, $C_{1-6}$alkyl, $C_{1-6}$alkoxy, and $C_{1-6}$alkoxy substituted by one or more fluorine atoms,
or a pharmaceutically acceptable salt, solvate, ester, or salt or solvate of such ester thereof.

2. The compound as claimed in claim 1 wherein $R^0$ and $R^1$ are independently H, halogen or $C_{1-4}$alkoxy; $R^2$ is CN or halogen; and $R^3$ is $C_{1-3}$alkyl or $NH_2$.

3. The compound as claimed in claim 1 wherein $R^0$ is F; $R^1$ is H; $R^2$ is CN or Br; and $R^3$ is methyl or $NH_2$.

4. The compound as claimed in claim 1 wherein $R^0$ is F; $R^1$ is H; $R^2$ is CN, Br or Cl; and $R^3$ is methyl or $NH_2$.

5. The compound as claimed in claim 1 wherein $R^0$ is at the 3- or 4-position of the phenyl ring and $R^2$ is at the 6-position of the pyrazolopyridine ring.

6. A compound selected from the group consisting of:
  4-[6-cyano-2-(4-fluorophenyl)pyrazolo[1,5-a]pyridin-3-yl]benzenesulfonamide;
  2-(4-fluorophenyl)-3-[4-(methylsulfonyl)phenyl] pyrazolo[1,5-a]pyridine-6-carbonitrile;
  4-[6-bromo-2-(4-fluorophenyl)pyrazolo[1,5-a]pyridin-3-yl]benzenesulfonamide,
  6-bromo-2-(4-fluorophenyl)-3-[4-(methylsulfonyl) phenyl]pyrazolo[1,5-a] pyridine;
or a pharmaceutically acceptable salt, solvate, ester, or salt or solvate of such ester thereof.

7. A compound selected from the group consisting of:
  4-[6-chloro-2-(4fluorophenyl)pyrazolo[1,5-a]pyridin-3-yl]benzenesulfonamide;
  4-[6-chloro-2-(4-ethoxyphenyl)pyrazolo[1,5-a]pyridin-3-yl]benzenesulfonamide;
  4-[6-chloro-2-(3-fluorophenyl)pyrazolo[1,5-a]pyridin-3-yl]benzenesulfonamide;
  4-[6-chloro-2-phenyl-pyrazolo[1,5-a]pyridin-3-yl] benzenesulfonamide;
or a pharmaceutically acceptable salt, solvate, ester, or salt or solvate of such ester thereof.

8. A pharmaceutical composition comprising a compound according to claim 1.

9. A method of treating a subject suffering from an inflammatory disorder, which method comprises administering to said subject an effective COX-2 inhibiting amount of a compound according to claim 1.

10. The compound according to claim 5 wherein $R^0$ is at the 4-position of the phenyl ring.

11. The pharmaceutical composition according to claim 8 further comprising one or more physiologically acceptable carriers or excipients.

12. The method according to claim 9, wherein said subject is a human.

13. A process for the preparation of a compound of formula (I) according to claim 1, comprising the steps of
  a) reacting a compound of formula (II)

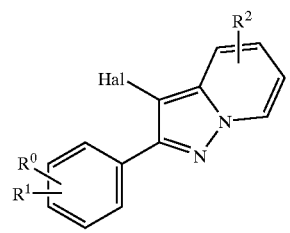

(II)

wherein Hal is halogen; with a compound of formula (III)

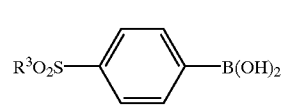

(III)

in the presence of a transition metal catalyst; and
  b) optionally converting the compound of formula (I) to a pharmaceutically acceptable salt, solvate, ester, or salt or solvate of such ester thereof.

14. A process for the preparation of a compound of formula (I) according to claim 1 wherein $R^3$ is $C_{1-4}$alkyl, said process comprising the steps of:

a) oxidizing a compound of formula (IV)

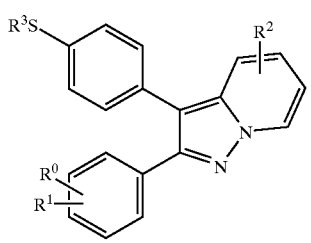

(IV)

and b) optionally converting the compound of formula (I) to a pharmaceutically acceptable salt, solvate, ester, or salt or solvate of such ester thereof.

15. A process for the preparation of a compound of formula (I) according to claim 1 wherein $R^2$ is halogen, said process comprising the steps of:

a) halogenating a compound of formula (V)

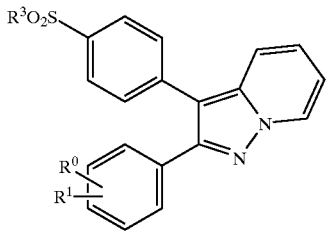

(V)

and b) optionally converting the compound of formula (I) to a pharmaceutically acceptable salt, solvate, ester, or salt or solvate of such ester thereof.

16. A process for the preparation of a compound of formula (I) according to claim 1 comprising the steps of:

a) reacting a compound of formula (VI)

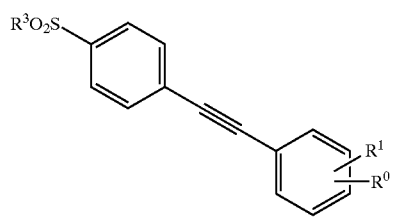

(VI)

with an aminopyridinium complex of formula (VII)

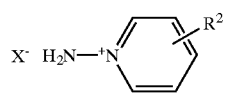

(VII)

wherein $X^-$ is a counterion; and b) optionally converting the compound of formula (I) to a pharmaceutically acceptable salt, solvate, ester, or salt or solvate of such ester thereof.

17. A process for the preparation of a compound of formula (I) according to claim 1 comprising the steps of:

a) reacting a compound of formula (II)

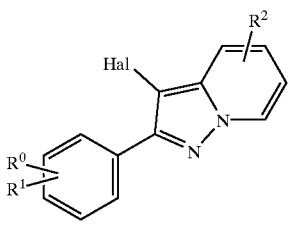

(II)

wherein Hal is a halogen; with a stanane of formula (XVII)

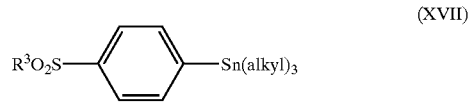

(XVII)

in the presence of a transition metal catalyst; and b) optionally converting the compound of formula (I) to a pharmaceutically acceptable salt, solvate, ester, or salt or solvate of such ester thereof.

18. A process for the preparation of a compound of formula (I) according to claim 1 where $R^3$ is $NH_2$, comprising the steps of:

a) reacting a compound of formula (XVIII)

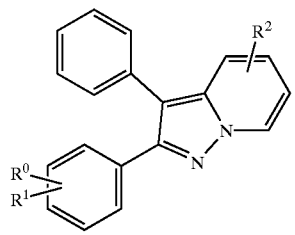

(XVIII)

with a source of ammonia under conventional conditions; and b) optionally converting the compound of formula (I) to a pharmaceutically acceptable salt, solvate, ester, or salt or solvate of such ester thereof.

19. A compound of formula (I)

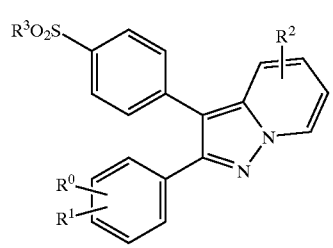

(I)

wherein $R^0$ and $R^1$ are independently selected from the group consisting of H, halogen, $C_{1-6}$alkyl, $C_{1-6}$alkoxy, and $C_{1-6}$alkoxy substituted by one or more fluorine atoms;

$R^2$ is halogen or CN; and $R^3$ is $C_{1-6}$alkyl or $NH_2$;

or a pharmaceutically acceptable salt, solvate, ester, or salt or solvate of such ester thereof.

20. A pharmaceutical composition comprising a compound according to claim 19.

21. A method of treating a subject suffering from a condition selected from the group consisting of pain, fever, and inflammation, which method comprises administering to said subject an effective COX-2 inhibiting amount of a compound according to claim 1.

22. A method of treating a subject suffering from a condition selected from the group consisting of rheumatic fever, symptoms associated with influenza or other viral infections, lower back pain, neck pain, headache, toothache, sprains, strains, myositis, neuropathic pain, synovitis, arthritis, rheumatoid arthritis, degenerative joint diseases, osteoarthritis, gout, ankylosing spondylitis, tendinitis, bursitis, psoriasis, eczema, burns, dermatitis, sports injuries, injuries arising from surgical and dental procedures, colonic cancer, stroke, epilepsy, epileptic seizures, dysmenorrhoea, premature labor, asthma, allergic rhinitis, respiratory distress syndrome, inflammatory bowel disease, Crohns disease, gastritis, irritable bowel syndrome, ulcerative colitis, inflammation in vascular disease, inflammation in migraine, inflammation in periarteritis, inflammation in nodosa, inflammation in thyroiditis, inflammation in aplastic anemia, inflammation in Hodgkin's disease, inflammation in scleroderma, inflammation in type I diabetes, inflammation in myasthenia gravis, inflammation in multiple sclerosis, inflammation in sorcoidosis, inflammation in nephrotic syndrome, inflammation in Bechet's syndrome, inflammation in polymyositis, inflammation in gingivitis, inflammation in conjunctivitis, inflammation in myocardial ischemia, retinitis, retinopathies, uveitis, acute injury to the eye tissue, dementia, degenerative dementia, vascular dementia, dementia associated with intracranial space occupying lesions, dementia associated with trauma, dementia associated with infections, dementia associated with metabolism, dementia associated with toxins, dementia associated with anoxia, dementia associated with vitamin deficiency, and mild cognitive impairment associated with aging, which method comprises administering to said subject an effective COX-2 inhibiting amount of a compound according to claim 1.

23. A method of treating a subject suffering from rhumatoid arthritis, which method comprises administering to said subject an effective COX-2 inhibiting amount of a compound according to claim 1.

24. A method of treating a subject suffering from osteoarthritis, which method comprises administering to said subject an effective COX-2 inhibiting amount of a compound according to claim 1.

25. A method of treating a subject suffering from pain, which method comprises administering to said subject an effective COX-2 inhibiting amount of a compound according to claim 1.

26. A method of treating a subject suffering from inflammation in multiple sclerosis, which method comprises administering to said subject an effective COX-2 inhibiting amount of a compound according to claim 1.

27. A method of treating a subject suffering from inflammation in migraine, which method comprises administering to said subject an effective COX-2 inhibiting amount of a compound according to claim 1.

28. A method of treating a subject suffering from an inflammatory disorder, which method comprises administering to said subject an effective COX-2 inhibiting amount of a compound according to claim 19.

29. A method of treating a subject suffering from a condition selected from the group consisting of pain, fever, and inflammation, which method comprises administering to said subject an effective COX-2 inhibiting amount of a compound according to claim 19.

30. A method of treating a subject suffering from a condition selected from the group consisting of rheumatic fever, symptoms associated with influenza or other viral infections, lower back pain, neck pain, headache, toothache, sprains, strains, myositis, neuropathic pain, synovitis, arthritis, rheumatoid arthritis, degenerative joint diseases, osteoarthritis, gout, ankylosing spondylitis, tendinitis, bursitis, psoriasis, eczema, burns, dermatitis, sports injuries, injuries arising from surgical and dental procedures, colonic cancer, stroke, epilepsy, epileptic seizures, dysmenorrhoea, premature labor, asthma, allergic rhinitis, respiratory distress syndrome, inflammatory bowel disease, Crohns disease, gastritis, irritable bowel syndrome, ulcerative colitis, inflammation in vascular disease, inflammation in migraine, inflammation in periarteritis, inflammation in nodosa, inflammation in thyroiditis, inflammation in aplastic anemia, inflammation in Hodgkin's disease, inflammation in scleroderma, inflammation in type I diabetes, inflammation in myasthenia gravis, inflammation in multiple sclerosis, inflammation in sorcoidosis, inflammation in nephrotic syndrome, inflammation in Bechet's syndrome, inflammation in polymyositis, inflammation in gingivitis, inflammation in conjunctivitis, inflammation in myocardial ischemia, retinitis, retinopathies, uveitis, acute injury to the eye tissue, dementia, degenerative dementia, vascular dementia, dementia associated with intracranial space occupying lesions, dementia associated with trauma, dementia associated with infections, dementia associated with metabolism, dementia associated with toxins, dementia associated with anoxia, dementia associated with vitamin deficiency, and mild cognitive impairment associated with aging, which method comprises administering to said subject an effective COX-2 inhibiting amount of a compound according to claim 19.

31. A method of treating a subject suffering from rhumatoid arthritis, which method comprises administering to said subject an effective COX-2 inhibiting amount of a compound according to claim 19.

32. A method of treating a subject suffering from osteoarthritis, which method comprises administering to said subject an effective COX-2 inhibiting amount of a compound according to claim 19.

33. A method of treating a subject suffering from pain, which method comprises administering to said subject an effective COX-2 inhibiting amount of a compound according to claim 19.

34. A method of treating a subject suffering from inflammation in multiple sclerosis, which method comprises administering to said subject an effective COX-2 inhibiting amount of a compound according to claim 19.

35. A method of treating a subject suffering from inflammation in migraine, which method comprises administering to said subject an effective COX-2 inhibiting amount of a compound according to claim 19.

\* \* \* \* \*

UNITED STATES PATENT AND TRADEMARK OFFICE
CERTIFICATE OF CORRECTION

PATENT NO. : 6,498,166 B1
DATED : August 7, 2001
INVENTOR(S) : Campbell et al.

It is certified that error appears in the above-identified patent and that said Letters Patent is hereby corrected as shown below:

Column 25,
Line 40, "A method of treating a subject suffering from rhuma-" should read
-- A method of treating a subject suffering from rheuma- --

Column 26,
Line 40, "A method of treating a subject suffering from rhuma-" should read
-- A method of treating a subject suffering from rheuma- --

Signed and Sealed this

Twenty-first Day of October, 2003

JAMES E. ROGAN
*Director of the United States Patent and Trademark Office*